(12) United States Patent
Tomioka

(10) Patent No.: US 9,306,112 B2
(45) Date of Patent: Apr. 5, 2016

(54) PHOTOCONDUCTIVE ANTENNA, TERAHERTZ WAVE GENERATING DEVICE, CAMERA, IMAGING DEVICE, AND MEASURING DEVICE

(71) Applicant: SEIKO EPSON CORPORATION, Tokyo (JP)

(72) Inventor: Hiroto Tomioka, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 1 day.

(21) Appl. No.: 13/717,835

(22) Filed: Dec. 18, 2012

(65) Prior Publication Data

US 2013/0153765 A1  Jun. 20, 2013

(30) Foreign Application Priority Data

Dec. 20, 2011  (JP) ................. 2011-278883

(51) Int. Cl.
| | |
|---|---|
| *H01L 31/00* | (2006.01) |
| *H01L 33/00* | (2010.01) |
| *H01L 31/16* | (2006.01) |
| *H01L 31/09* | (2006.01) |
| *H01L 27/144* | (2006.01) |
| *G01S 17/89* | (2006.01) |
| *H01L 27/146* | (2006.01) |
| *G01N 21/3581* | (2014.01) |
| *G01S 13/89* | (2006.01) |

(52) U.S. Cl.
CPC ............. *H01L 33/0004* (2013.01); *G01S 17/89* (2013.01); *H01L 27/1446* (2013.01); *H01L 27/14603* (2013.01); *H01L 27/14625* (2013.01); *H01L 31/09* (2013.01); *H01L 31/16* (2013.01); *G01N 21/3581* (2013.01); *G01S 13/89* (2013.01)

(58) Field of Classification Search
USPC ......................................................... 250/330
See application file for complete search history.

(56) References Cited

U.S. PATENT DOCUMENTS

| 4,356,210 | A | 10/1982 | Imai et al. |
| 4,435,443 | A | 3/1984 | Imai et al. |
| 4,933,731 | A * | 6/1990 | Kimura ........................ 257/438 |
| 8,274,058 | B1 * | 9/2012 | Wanke et al. ............ 250/370.12 |
| 2010/0244993 | A1 * | 9/2010 | Sekiguchi et al. ......... 333/219.1 |
| 2011/0176246 | A1 | 7/2011 | Kim et al. |

FOREIGN PATENT DOCUMENTS

| JP | 52-064287 A | 5/1977 |
| JP | 55-019854 A | 2/1980 |
| JP | 2004-266057 A | 9/2004 |

(Continued)

*Primary Examiner* — David Porta
*Assistant Examiner* — Edwin Gunberg
(74) *Attorney, Agent, or Firm* — Global IP Counselors, LLP

(57) ABSTRACT

A photoconductive antenna is adapted to generate terahertz waves when irradiated by pulsed light. The photoconductive antenna includes first and second conductive layers, a semiconductor layer positioned between the first and second conductive layers, first and second electrodes, and a dielectric layer. The semiconductor layer is made of a semiconductor material having a carrier density that is lower than a carrier density of the semiconductor material of the first conductive layer or the second conducive layer. The first and second electrodes are electrically connected to the first and second conductive layers, respectively. The second electrode has an aperture through which the pulsed light passes. The dielectric layer is made of a dielectric material, and is in contact with a surface of the semiconductor layer having a normal direction extending orthogonal to a lamination direction of the first conductive layer, the semiconductor layer, and the second conductive layer.

21 Claims, 9 Drawing Sheets

(56) References Cited

FOREIGN PATENT DOCUMENTS

| | | | |
|---|---|---|---|
| JP | 2006-302919 | A | 11/2006 |
| JP | 2006-313803 | A | 11/2006 |
| JP | 2007-300022 | A | 11/2007 |
| JP | 2011-176246 | A | 9/2011 |

* cited by examiner

PHOTOCONDUCTIVE ANTENNA, TERAHERTZ WAVE GENERATING DEVICE, CAMERA, IMAGING DEVICE, AND MEASURING DEVICE

CROSS-REFERENCE TO RELATED APPLICATIONS

This application claims priority to Japanese Patent Application No. 2011-278883 filed on Dec. 20, 2011. The entire disclosure of Japanese Patent Application No. 2011-278883 is hereby incorporated herein by reference.

BACKGROUND

1. Technical Field

The present invention relates to a photoconductive antenna, a terahertz wave generating device, a camera, an imaging device, and a measuring device.

2. Related Art

In recent years, attention has been devoted to terahertz waves, which are electromagnetic waves with frequencies of 100 GHz or greater and 30 THz or less. Terahertz waves can be used in various forms of measurement and non-destructive testing such as imaging and spectrometry.

The terahertz wave generating device that generates these terahertz waves has a light source device that generates light pulses (pulsed light) having pulse widths at the approximately sub picosecond level (several hundred femtoseconds) and a photoconductive antenna that generates terahertz waves by irradiating light pulses generated by the light pulse generator.

As the photoconductive antenna, for example, disclosed in Patent Document 1 is a terahertz wave generating device (photoconductive antenna) having a laminated body (pin structure) for which an n type semiconductor layer, an i type semiconductor layer, and a p type semiconductor layer are laminated in that order. With this photoconductive antenna, when light pulses are irradiated on the p type semiconductor layer via an aperture formed on an electrode provided on the p type semiconductor layer, terahertz waves are emitted radially from the entire side surface of the i type semiconductor layer.

With the photoconductive antenna noted in Patent Document 1, for a dipole shaped photoconductive antenna (PCA) using a low temperature growth GaAs (LT-GaAs) substrate, it is possible to make the intensity of the generated terahertz waves approximately 10 times larger.

However, with the photoconductive antenna noted in Japanese Laid-Open Patent Application Publication No. 2007-300022, terahertz waves with no directionality are generated, so there is a great deal of waste, and the intensity of the terahertz waves irradiated at the target site was insufficient.

SUMMARY

An object of the present invention is to provide a photoconductive antenna capable of generating terahertz waves with directionality, a terahertz wave generating device, a camera, an imaging device, and a measuring device.

This kind of object is achieved by the aspects of the present invention noted hereafter.

A photoconductive antenna according to one aspect of the present invention is adapted to generate terahertz waves when irradiated by pulsed light. The photoconductive antenna includes a first conductive layer, a second conductive layer, a semiconductor layer, a first electrode, a second electrode, and a dielectric layer. The first conductive layer is made of a semiconductor material containing a first conductive type impurity. The second conductive layer is made of a semiconductor material containing a second conductive type impurity different from the first conductive type impurity. The semiconductor layer is positioned between the first conductive layer and the second conductive layer, and is made of a semiconductor material having a carrier density that is lower than a carrier density of the semiconductor material of the first conductive layer or a carrier density of the semiconductor material of the second conducive layer. The first electrode is electrically connected to the first conductive layer. The second electrode is electrically connected to the second conductive layer, and has an aperture through which the pulsed light passes. The dielectric layer is made of a dielectric material, and is in contact with a surface of the semiconductor layer having a normal direction extending orthogonal to a lamination direction of the first conductive layer, the semiconductor layer, and the second conductive layer.

With this configuration, the terahertz waves have the property of trying to advance in a substance of a higher dielectric constant, so terahertz waves generated by the semiconductor layer are led in a designated direction by the dielectric layer, and by doing that, it is possible to generate terahertz waves having directionality. As a result, it is possible to generate terahertz waves with higher intensity than conventionally.

With the photoconductive antenna of the above mentioned aspect of the present invention, a relative dielectric constant of the dielectric material is preferably higher than a relative dielectric constant of the semiconductor material of the semiconductor layer.

With this configuration, it is possible for the terahertz waves to be led efficiently by the dielectric layer.

With the photoconductive antenna of the above mentioned aspect of the present invention, a width of a part of the dielectric layer as viewed along the lamination direction preferably increases as a distance from the semiconductor layer increases.

With this configuration, it is possible for the terahertz waves to be led efficiently by the dielectric layer.

The photoconductive antenna of the above mentioned aspect of the present invention preferably further includes a covering layer covering a part of the surface of the semiconductor layer which is not in contact with the dielectric layer.

With this configuration, it is possible to prevent corrosion of the semiconductor layer.

The photoconductive antenna of the above mentioned aspect of the present invention preferably further includes a first reflective layer in contact with a bottom surface of the dielectric layer, and configured and arranged to reflect the terahertz waves.

With this configuration, by being reflected by the first reflective layer, it is possible to prevent the terahertz waves advancing through the dielectric layer from passing through the dielectric layer before reaching the emission unit that emits the terahertz waves of the dielectric layer.

With the photoconductive antenna of the above mentioned aspect of the present invention, the first electrode is preferably configured and arranged to reflect the terahertz waves.

With this configuration, it is possible to simplify the structure and to make manufacturing easier.

The photoconductive antenna of the above mentioned aspect of the present invention preferably further includes a second reflective layer in contact with a top surface of the dielectric layer, and configured and arranged to reflect the terahertz waves.

With this configuration, by being reflected by the second reflective layer, it is possible to prevent the terahertz waves advancing through the dielectric layer from passing through the dielectric layer before reaching the emission unit that emits the terahertz waves of the dielectric layer.

With the photoconductive antenna of the above mentioned aspect of the present invention, the second electrode is preferably configured and arranged to reflect the terahertz waves.

With this configuration, it is possible to simplify the structure and to make manufacturing easier.

With the photoconductive antenna of the above mentioned aspect of the present invention, the second conductive layer preferably includes a thin walled part having a thickness in the lamination direction that is thinner than a part of the second conductive layer disposed outside of the aperture as viewed along the lamination direction.

With this configuration, it is possible to suppress the pulsed light from being absorbed by the second conductive layer, and possible to set the site positioned at outside the aperture of the second conductive layer to an appropriate value.

With the photoconductive antenna of the above mentioned aspect of the present invention, the semiconductor material of the semiconductor layer is preferably a III-V compound.

With this configuration, it is possible to generate high intensity terahertz waves.

A terahertz wave generating device according to another aspect of the present invention includes the photoconductive antenna according to the above mentioned aspects, and a light source configured and arranged to generate the pulsed light.

With this configuration, it is possible to provide a terahertz wave generating device having the effects of the present invention.

A camera according to another aspect of the present invention includes the photoconductive antenna according to the above mentioned aspects, a light source configured and arranged to generate the pulsed light, and a terahertz wave detecting unit configured and arranged to detect the terahertz waves emitted from the photoconductive antenna and reflected by an object.

With this configuration, it is possible to provide a camera having the effects of the invention.

An imaging device according to another aspect of the present invention includes the photoconductive antenna according to the above mentioned aspects, a light source configured and arranged to generate the pulsed light, a terahertz wave detecting unit configured and arranged to detect the terahertz waves emitted from the photoconductive antenna and transmitted through an object or reflected by the object, and an image forming unit configured and arranged to generate an image of the object based on detection results of the terahertz wave detecting unit.

With this configuration, it is possible to provide an imaging device having the effects of the present invention.

A measuring device according to another aspect of the present invention includes the photoconductive antenna according to the above mentioned aspects, a light source configured and arranged to generate the pulsed light, a terahertz wave detecting unit configured and arranged to detect the terahertz waves emitted from the photoconductive antenna and transmitted through an object or reflected by the object, and a measuring unit configured and arranged to measure the object based on detection results of the terahertz wave detecting unit.

With this configuration, it is possible to provide a measuring device having the effects of the present invention.

BRIEF DESCRIPTION OF THE DRAWINGS

Referring now to the attached drawings which form a part of this original disclosure.

DETAILED DESCRIPTION OF EXEMPLARY EMBODIMENTS

Detailed description of the photoconductive antenna, the terahertz wave generating device, the camera, the imaging device, and the measuring device of the present invention will be provided based on preferred embodiments shown in the attached drawings.

First Embodiment

Figure 1:
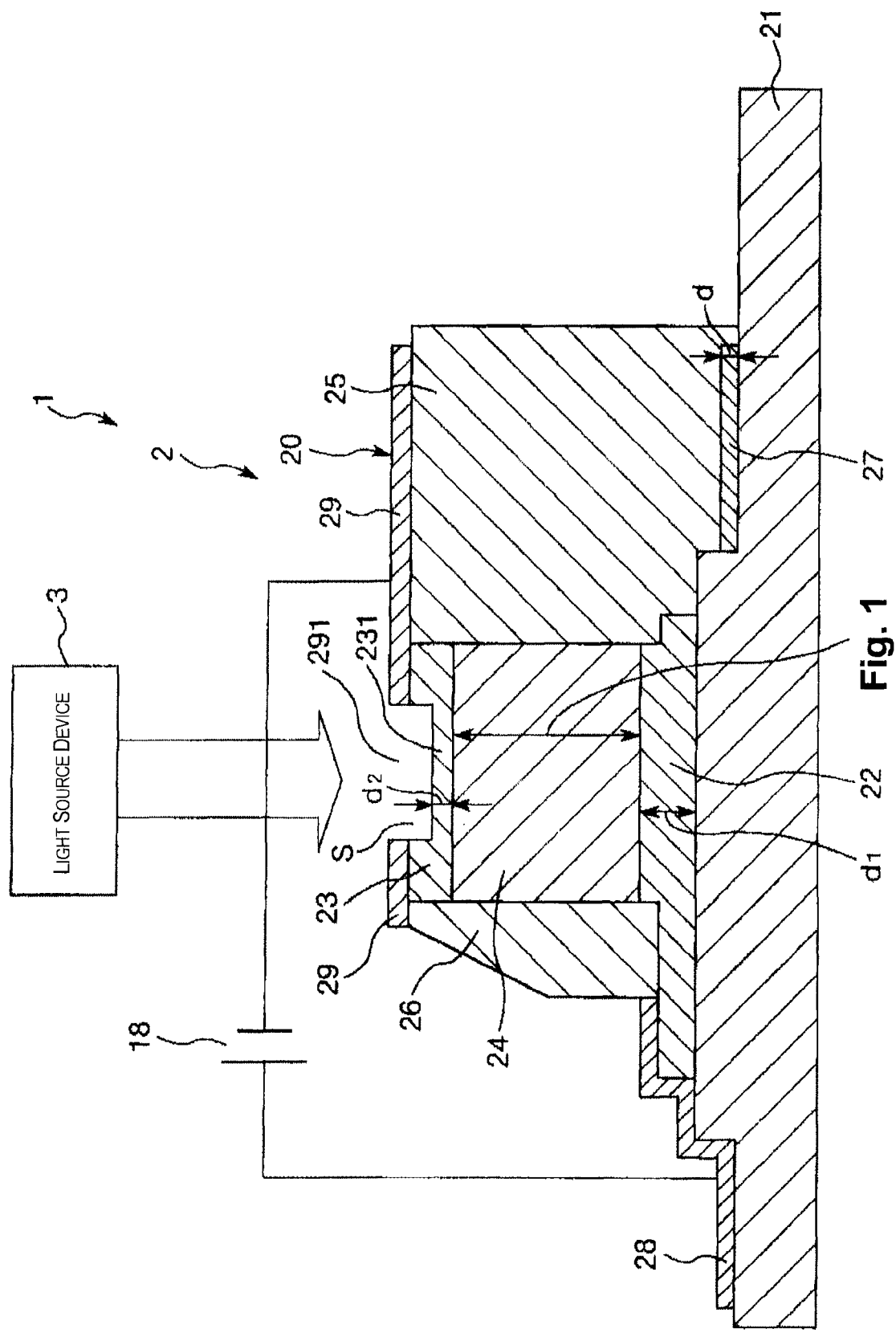
FIG. 1 is a cross section view taken along a line S-S in FIG. 2, showing an embodiment of the terahertz wave generating device of the present invention.
Figure 2:
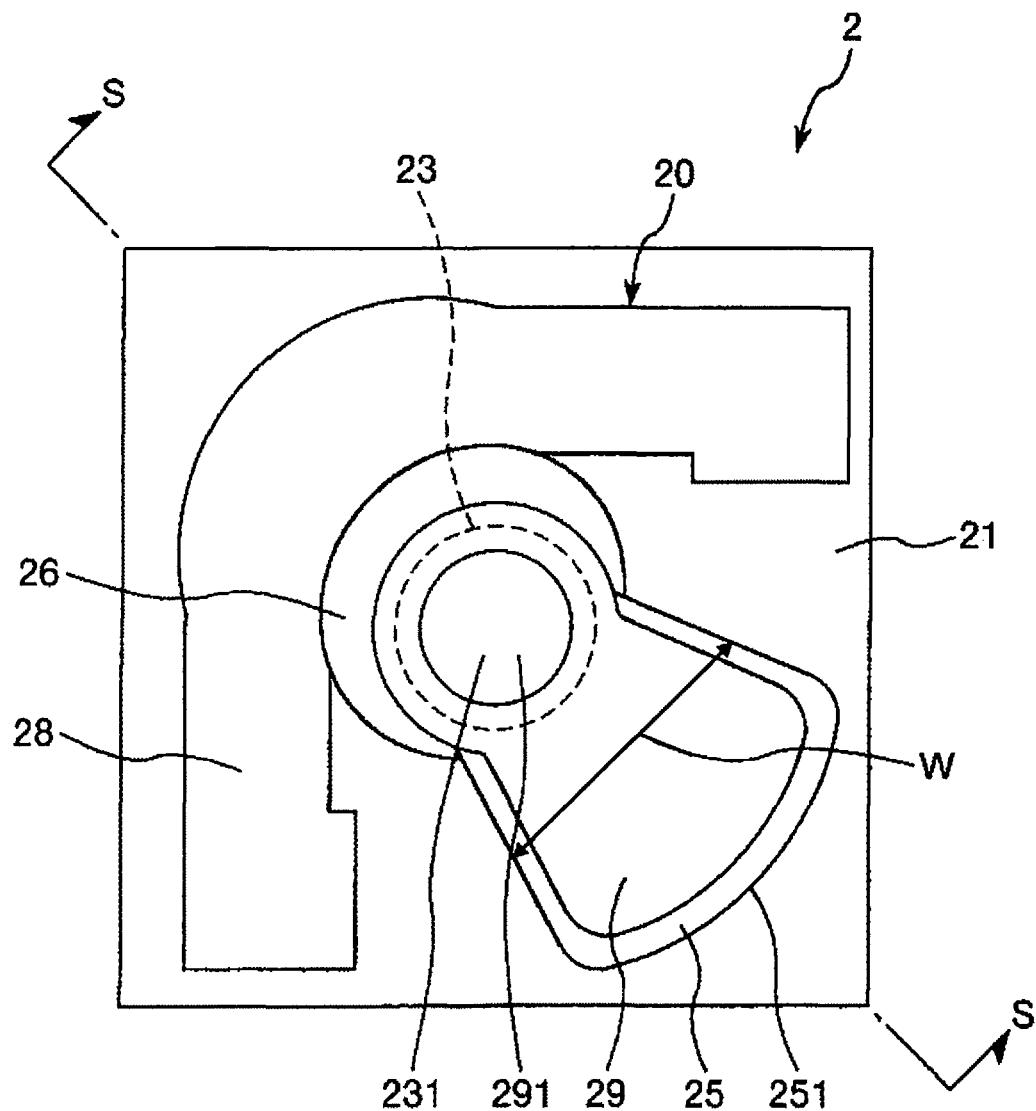
FIG. 2 is a plan view of the photoconductive antenna of the terahertz wave generating device shown in FIG. 1.
Figure 3:
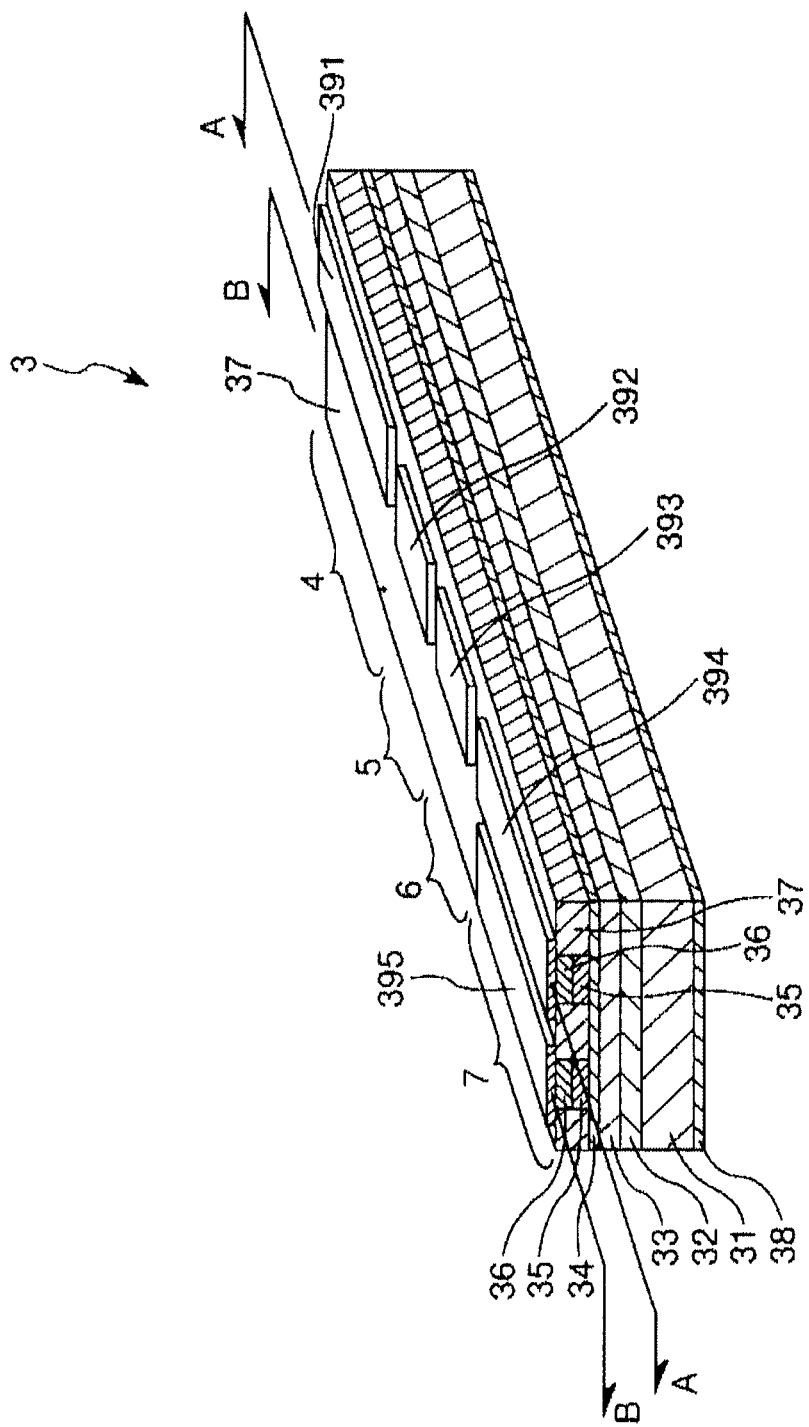
FIG. 3 is a cross section perspective view of the light source device of the terahertz wave generating device shown in FIG. 1.
Figure 4:
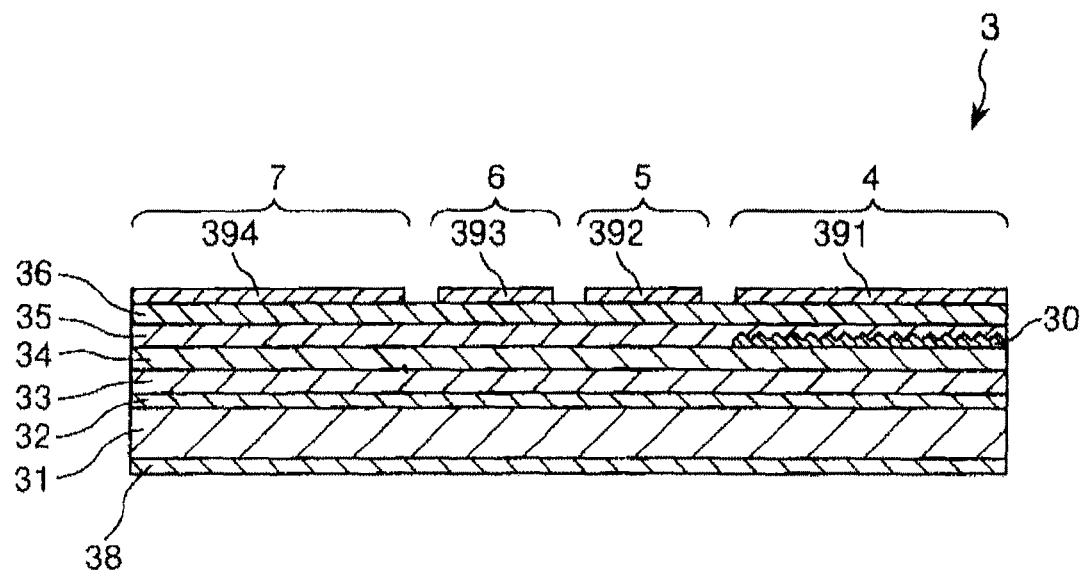
FIG. 4 is a cross section view taken along a line A-A in FIG. 3.
Figure 5:
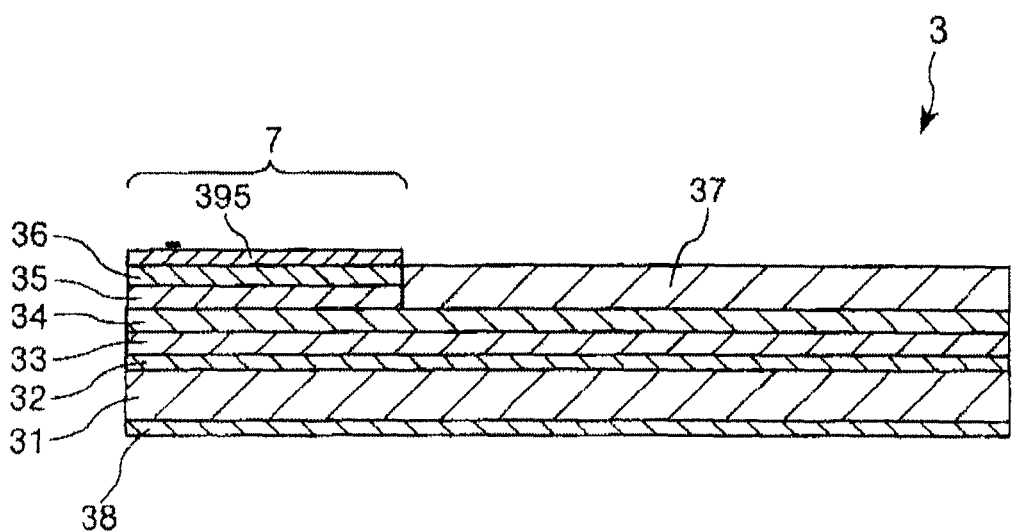
FIG. 5 is a cross section view taken along a line B-B in FIG. 3.

FIG. 1 is a drawing showing an embodiment of the terahertz wave generating device of the present invention. With this FIG. 1, a cross section view of line S-S in FIG. 2 is shown for the photoconductive antenna, and a block diagram is shown for the light source device. FIG. 2 is a plan view of the photoconductive antenna of the terahertz wave generating device shown in FIG. 1. FIG. 3 is a cross section perspective view of the light source device of the terahertz wave generating device shown in FIG. 1. FIG. 4 is a cross section view of line A-A in FIG. 3. FIG. 5 is a cross section view of line B-B in FIG. 3. Note that hereafter, in FIG. 1 and FIG. 3 to FIG. 5, the upper side will be described as "upper" and the lower side will be described as "lower."

As shown in FIG. 1, the terahertz wave generating device 1 has a light source device 3 that generates light pulses (pulsed light) which is excitation light, and a photoconductive antenna 2 for generating terahertz waves by irradiating light pulses generated by the light source device 3. A terahertz wave means an electromagnetic wave for which the frequency is 100 GHz or greater and 30 THz or less, and particularly an electromagnetic wave of 300 GHz or greater and 3 THz or less.

As shown in FIG. 3 to FIG. 5, with this embodiment, the light source device 3 has a light pulse generator 4 that generates light pulses, a first pulse compressor 5 that performs pulse compression on light pulses generated by the light pulse generator 4, a second pulse compressor 7 that performs pulse compression on light pulses for which pulse compression was done by the first pulse compressor 5, and an amplifier 6 that amplifies the light pulses.

The amplifier 6 can be provided at the front stage of the first pulse compressor 5, or between the first pulse compressor 5 and the second pulse compressor 7, but with the configuration in the drawing, the amplifier 6 is provided between the first pulse compressor 5 and the second pulse compressor 7. With this configuration, the light pulses which underwent pulse compression by the first pulse compressor 5 are amplified by the amplifier 6, and the light pulses amplified by the amplifier 6 undergo pulse compression by the second pulse compressor 7.

Also, the pulse width (half-value width) of the light pulses emitted from the light source device 3 is not particularly restricted, but is preferably 1 femtosecond or greater and 800 femtoseconds or less, and more preferably 10 femtoseconds or greater and 200 femtoseconds or less.

Also, the frequency of the light pulses emitted from the light source device 3 is set to the same or greater frequency corresponding to the band gap of the i type semiconductor layer 24 of the photoconductive antenna 2 described later.

Also, the light pulse generator 4 can use a so-called semiconductor laser such as a DBR laser, DFB laser, mode locked laser or the like, for example. The pulse width of the light pulses generated by this light pulse generator 4 is not particularly restricted, but is preferably 1 picosecond or greater and 100 picoseconds or less.

Also, the first pulse compressor 5 performs pulse compression based on saturable absorption. Specifically, the first pulse compressor 5 has a saturable absorber, and using that saturable absorber, light pulses are compressed and pulse width is decreased.

Also, the second pulse compressor 7 performs pulse compression based on group velocity dispersion compensation. Specifically, the second pulse compressor 7 has a group velocity dispersion compensation medium, and with this embodiment a coupled waveguide structure, and using that coupled waveguide structure, light pulses are compressed and pulse width is decreased.

Also, the light pulse generator 4 of the light source device 3, the first pulse compressor 5, the amplifier 6, and the second pulse compressor 7 are laminated as an integral unit, specifically, on the same substrate.

In specific terms, the light source device 3 has a substrate 31 which is a semiconductor substrate, a cladding layer 32 which is provided on the substrate 31, an active layer 33 which is provided on the cladding layer 32, a waveguide structure processing etching stop layer 34 provided on the active layer 33, a cladding layer 35 provided on the waveguide structure processing etching stop layer 34, a contact layer 36 provided on the cladding layer 35, an insulating layer 37 provided on the waveguide structure processing etching stop layer 34, a cladding layer 32 side electrode 38 provided on the surface of the substrate 31, and cladding layer 35 side electrodes 391, 392, 393, 394, and 395 provided on the contact layer 36 and the insulating layer 37 surface. Also, a diffraction grating 30 is provided between the waveguide structure processing etching stop layer 34 of the light pulse generator 4 and the cladding layer 35. Note that the waveguide structure processing etching stop layer is not limited to being provided directly above the active layer, but can also be provided within the cladding layer, for example.

The structural materials of each part are not particularly restricted, but an example for the substrate 31 and the contact layer 36 is GaAs or the like. Also, an example for the cladding layers 32 and 35, the waveguide structure processing etching stop layer 34, and the diffraction grating 30 includes AlGaAs or the like. Also, for the active layer 33, an example is a structure using a quantum effect called a multiple quantum well or the like. In specific terms, an example of the active layer 33 is an item with a structure called a distributed index of refraction multiple quantum well structured with multiple quantum wells or the like made by alternately providing a plurality of well layers (GaAs well layers) and barrier layers (AlGaAs barrier layers) or the like.

With the constitution in the drawing, the waveguide of the light source device 3 is constituted from the cladding layer 32, the active layer 33, the waveguide structure processing etching stop layer 34, and the cladding layer 35. Also, the cladding layer 35 is provided in a shape corresponding to the waveguide, only on the top part of the waveguide. Also, the cladding layer 35 is formed by removal of the unnecessary parts by etching. Depending on the manufacturing method, it is possible to omit the waveguide structure processing etching stop layer 34.

Also, two each of the cladding layer 35 and the contact layer 36 are provided. One of the cladding layer 35 and the contact layer 36 constitute the light pulse generator 4, the first pulse compressor 5, the amplifier 6, and part of the second pulse compressor 7, and are provided sequentially, and the other cladding layer 35 and contact layer 36 constitute part of the second pulse compressor 7. Specifically, one pair of cladding layers 35 and one pair of contact layers 36 are provided on the second pulse compressor 7.

Also, the electrode 391 is provided so as to correspond to the cladding layer 35 of the light pulse generator 4, the electrode 392 is provided so as to correspond to the cladding layer 35 of the first pulse compressor 5, the electrode 393 is provided so as to correspond to the cladding layer 35 of the amplifier 6, and the electrodes 394 and 395 are provided so as to respectively correspond to the two cladding layers 35 of the second pulse compressor 7. The electrode 38 is a shared electrode of the light pulse generator 4, the first pulse compressor 5, the amplifier 6, and the second pulse compressor 7. Then, the pair of electrodes of the light pulse generator 4 is constituted by the electrode 38 and the electrode 391, the pair of electrodes of the first pulse compressor 5 is constituted by the electrode 38 and the electrode 392, the pair of electrodes of the amplifier 6 is constituted by the electrode 38 and the electrode 393, and the two pairs of electrodes of the second pulse compressor 7 are constituted by the electrode 38 and electrode 394 and the electrode 38 and electrode 395.

The overall shape of the light source device 3 is a rectangular solid with the constitution in the drawing, but naturally it is not restricted to this.

Also, the dimensions of the light source device 3 are not particularly restricted, but for example can be 1 mm or greater and 10 mm or less×0.5 mm or greater and 5 mm or less×0.1 mm or greater and 1 mm or less.

With the present invention, it also goes without saying that the constitution of the light source device is not restricted to the previously described constitution.

Next, we will describe the photoconductive antenna 2.

As shown in FIG. 1 and FIG. 2, the photoconductive antenna 2 has a substrate 21 and a photoconductive antenna main unit 20 provided on the substrate 21.

The substrate 21 is not restricted provided it is an item that can support the photoconductive antenna main unit 20, and though it is possible to use a semiconductor substrate constituted by various types of semiconductor material, a resin substrate constituted by various types of resin material, or a glass substrate constituted by various types of glass material, a semiconductor substrate is preferable. Also, when using a semiconductor substrate as the substrate 21, as its semiconductor material, though not particularly restricted, it is possible to use various types of items, but a III-V compound semiconductor is preferable. Also, as the III-V compound semiconductor, though not particularly restricted, examples include GaAs, InP, InAs, InSb and the like.

Also, with the configuration in the drawing, the shape of the substrate 21 is rectangular when seen from the lamination direction (as viewed along the lamination direction) of the n type semiconductor layer 22, the i type semiconductor layer 24, and the p type semiconductor layer 23 described later. The shape of the substrate 21 is not restricted to being rectangular, and can also be a circle, an oval, or another polygon or the like such as a triangle, a pentagon, a hexagon or the like. Hereafter, "when seen from the lamination direction of the n type semiconductor layer 22, the i type semiconductor layer 24, and the p type semiconductor layer 23" is also called "the planar view." Also, "the lamination direction of the n type semiconductor layer 22, the i type semiconductor layer 24, and the p type semiconductor layer 23" is also simply stated as "the lamination direction."

The photoconductive antenna main unit 20 has an n type semiconductor layer (first conductive layer) 22, an i type semiconductor layer (semiconductor layer) 24 that generates terahertz waves, a p type semiconductor layer (second conductive layer) 23, a dielectric layer 25, a covering layer 26, a reflective layer (first reflective layer) 27 that reflects terahertz waves, and an electrode (first electrode) 28 and an electrode (second electrode) 29 constituting the pair of electrodes.

In this case, on the substrate 21, the n type semiconductor layer 22, the i type semiconductor layer 24, and the p type semiconductor layer 23 are laminated (provided) in that order from the substrate 21 side. Specifically, on the substrate 21 is formed a laminated body (pin structure) for which the n type semiconductor layer, the i type semiconductor layer, and the p type semiconductor layer are laminated in that order from the substrate 21 side. To say this yet another way, the i type semiconductor layer 24 is formed sandwiched by the n type semiconductor layer 22 and the p type semiconductor layer 23.

Also, the electrode 28 is provided on the substrate 21 and the n type semiconductor layer 22. Specifically, the electrode 28 is in contact with the n type semiconductor layer 22 and is electrically connected to the n type semiconductor layer 22.

Also, the electrode 29 is provided on the p type semiconductor layer 23 and the dielectric layer 25. Specifically, the electrode 29 is in contact with the p type semiconductor layer 23, and is electrically connected to the p type semiconductor layer 23. Also, the electrode 29 is in contact with the surface on the side opposite to the substrate 21 of the dielectric layer 25 (the top surface of the dielectric layer 25) from the lamination direction, and also acts as the second reflective layer that reflects terahertz waves. By providing the second reflective layer, the terahertz waves that are leaked from the top surface of the dielectric layer 25 (surface on the side opposite the substrate 21 of the dielectric layer 25) are reflected to inside the dielectric layer 25, and it is possible to efficiently lead the terahertz waves. It also goes without saying that it is possible to provide the second reflective layer separately from the electrode 29.

Also, the electrode 29 has an aperture 291 provided at a site corresponding to the p type semiconductor layer 23. With the aperture 291, the surface of the side opposite the i type semiconductor layer 24 of the p type semiconductor layer 23 is exposed. Then, with this terahertz wave generating device 1, the light pulses generated by the light source device 3 are irradiated on the p type semiconductor layer 23 via the aperture 291. Therefore, the window part through which the light pulses pass (are transmitted) is constituted by the aperture 291. It is also possible to provide on the aperture 291 a light permeable protective layer (not illustrated) through which light pulses can be transmitted.

Also, with the configuration in the drawing, the shape of the aperture 291 is circular with a planar view. The shape of the aperture 291 is not restricted to being a circle, and can also be an oval, or another polygon such as a triangle, a quadrangle, a pentagon, a hexagon or the like, for example.

Also, the surface area S of the aperture 291 with a planar view is not particularly restricted, and is an item set as appropriate according to various conditions, but is preferably 1 $\mu m^2$ or greater and 10000 $\mu m^2$ or less, and more preferably 10 $\mu m^2$ or greater and 100 $\mu m^2$ or less.

When the surface area S of the aperture 291 is smaller than the lower limit noted above, depending on other conditions, it may not be possible to condense the light pulses only on the site of that aperture 291, so light pulses are wasted, and when the upper limit value noted above is exceeded, depending on other conditions, the terahertz waves generated within a plurality of regions within the i type semiconductor layer 24 may interfere with each other.

Also, the dielectric layer 25 is provided on the substrate 21. This dielectric layer 25 is in contact with the part of the i type semiconductor layer 24 at the side surface of the laminated body, specifically, the surface of the i type semiconductor layer 24 having a normal line perpendicular to the lamination direction. The side surface of the laminated body can also be called the surface of the i type semiconductor layer 24 exposed between the n type semiconductor layer 22 and the p type semiconductor layer 23, or the surface of the i type semiconductor layer 24 that is not in contact with the n type semiconductor layer 22 and the p type semiconductor layer 23.

Also, a covering layer 26 is provided on the substrate 21 and the n type semiconductor layer 22. This covering layer 26 is in contact with (covers) the parts not contacted by the dielectric layer 25 among the parts of the i type semiconductor layer 24 on the side surface of the laminated body. With this configuration, the part of the i type semiconductor layer 24 on the side surface of the laminated body is covered by the dielectric layer 25 and the covering layer 26. With this configuration, it is possible to prevent corrosion or the like of the i type semiconductor layer 24.

Also, the reflective layer 27 is provided on the substrate 21, and is in contact with the surface of the substrate 21 side of the dielectric layer 25 (the bottom surface of the dielectric layer 25) from the lamination direction. Specifically, the reflective layer 27 is interposed between the substrate 21 and the dielectric layer 25. In other words, the dielectric layer 25 is sandwiched from the lamination direction by the reflective layer 27 and the electrode 29 which is the previously described second reflective layer. By providing this reflective layer 27, it is possible to reflect into the dielectric layer 25 the terahertz waves leaked from the bottom surface of the dielectric layer 25 to the substrate 21 side, and with this configuration, it is possible to efficiently lead the terahertz waves. Note that though the reflective layer 27 is constituted by the aforementioned electrode 28, it goes without saying that the electrode 28 can also act as the first reflective layer.

Also, the thickness d of the reflective layer 27 is not particularly restricted, and is set as appropriate according to various conditions, but it is preferably 10 mm or greater and 500 mm or less, and more preferably 30 mm or greater and 300 mm or less.

When the thickness d of the reflective layer 27 is less than the aforementioned lower limit value, depending on other conditions, the terahertz waves may be absorbed by the reflective layer 27, and when it exceeds the aforementioned upper limit value, depending on other conditions, the reflective layer 27 may become an obstacle.

The n type semiconductor layer 22 is constituted from a semiconductor material containing an n type (first conductive type) impurity. The carrier density (impurity concentration) of the n type semiconductor layer 22 is preferably $1\times10^{17}/cm^3$ or greater, more preferably $1\times10^{20}/cm^3$ or greater, and even more preferably $1\times10^{20}/cm^3$ or greater and $1\times10^{25}/cm^3$ or less. The n type impurity is not particularly restricted, but examples include Si, Ge, S, Se or the like.

Also, the thickness d1 of the n type semiconductor layer 22 is not particularly restricted, and is set as appropriate according to various conditions, but is preferably 1 μm or greater and 4 mm or less, and more preferably 1 μm or greater and 10 μm or less.

Also, the p type semiconductor layer 23 is constituted by a semiconductor material containing a p type (second conductive type) impurity. The carrier density of the p type semiconductor layer 23 is preferably $1\times10^{17}/cm^3$ or greater, more preferably $1\times10^{20}/cm^3$ or greater, and even more preferably $1\times10^{20}/cm^3$ or greater and $1\times10^{25}/cm^3$ or less. This p type impurity is not particularly restricted, but examples include Zn, Mg, C or the like.

Also, with a planar view, the p type semiconductor layer 23 has a thin walled part 231 positioned inside the aperture 291 of the electrode 29, for which the thickness is thinner than the site positioned at the outside of the aperture 291 of the p type semiconductor layer 23. With this configuration, it is possible to suppress light pulses from being absorbed by the p type semiconductor layer 23, and it is possible to set the thickness of the site positioned at the outside of the aperture 291 of the p type semiconductor layer 23 to a suitable value.

Also, the thickness d2 of the thin walled part 231 of the p type semiconductor layer 23 is not particularly restricted, and is set as appropriate according to various conditions, but is preferably 1 μm or greater and 2 mm or less, and more preferably 1 μm or greater and 10 μm or less.

Also, the i type semiconductor layer 24 is constituted with a semiconductor material. The semiconductor material constituting this i type semiconductor layer 24 is preferably an intrinsic semiconductor, but may also include a small volume of an n type impurity or a p type impurity.

To say this another way, the i type semiconductor layer 24 can be said to have a carrier density lower than an n type semiconductor layer 22 when it contains an n type impurity, and can be said to have a carrier density lower than a p type semiconductor when it contains a p type impurity. When the i type semiconductor layer 24 contains either the n type impurity or the p type impurity, the carrier density is lower than with the n type semiconductor layer 22 and the p type semiconductor layer 23.

In specific terms, the carrier density of the i type semiconductor layer 24 is preferably $1\times10^{18}$ $cm^3$ or less, more preferably $1\times10^{12}/cm^3$ or greater and $1\times10^{18}/cm^3$ or less, and even more preferably $1\times10^{12}/cm^3$ or greater and $1\times10^{15}/cm^3$ or less.

Also, the thickness d3 of the i type semiconductor layer 24 is not particularly restricted, and is set as appropriate according to various conditions, but is preferably 1 μm or greater and 4 mm or less, and more preferably 1 μm or greater and 10 μm or less.

If the thickness d3 of the i type semiconductor layer 24 is less than the lower limit value noted above, forming of the i type semiconductor layer 24 may be difficult depending on other conditions, and if it exceeds the upper limit value noted above, the withstand voltage may be insufficient depending on other conditions, so it is not possible to form an electric field of a large field intensity inside the i type semiconductor layer 24, and because of that, it is not possible to generate high intensity terahertz waves.

The semiconductor material of the p type semiconductor layer 23, the n type semiconductor layer 22, and the i type semiconductor layer 24 is not particularly restricted, and it is possible to use various types of item, but it is preferable to use a III-V compound semiconductor. Also, the III-V compound semiconductor is not particularly restricted, and examples include GaAs, InP, InAs, InSb and the like, for example.

Also, the dielectric layer 25 is constituted with a dielectric material, and has the function of leading the terahertz waves generated by the i type semiconductor layer 24 in a designated direction. The relative dielectric constant (dielectric constant) of the dielectric material constituting this dielectric layer 25 is preferably higher than the relative dielectric constant of the semiconductor material constituting the i type semiconductor layer 24. The terahertz waves have the property of trying to advance in substances with higher dielectric constants. Therefore, the terahertz waves generated by the i type semiconductor layer 24 are made incident from the side surface of that i type semiconductor layer 24 to the dielectric layer 25, and advance into that dielectric layer 25. In this way, the terahertz waves generated by the i type semiconductor layer 24 are led in a designated direction by the dielectric layer 25, and with this configuration, it is possible to generate high intensity terahertz waves which have directionality.

Also, the shape of the dielectric layer 25 is not particularly restricted, but with the configuration in the drawing, with the planar view, has a shape for which the center side part of a fan shape (the part including the intersection of the two straight lines constituting the outer form of the fan shape) is removed, and the shape of the emission unit 251 that emits terahertz waves of the dielectric layer 25 is an arc shape with a planar view. Specifically, with the planar view, the width W of the dielectric layer 25 gradually increases as it goes from the proximal side toward the distal side in relation to the i type semiconductor layer 24 (as the separation from the i type semiconductor layer 24 increases). With this configuration, it is possible to have the terahertz waves efficiently led by the dielectric layer 25.

It is also possible to have the width W of only a portion of the dielectric layer 25 gradually increase going from the proximal side toward the distal side in relation to the i type semiconductor layer 24. Specifically, with the planar view, the dielectric layer 25 is acceptable providing it has a part for which the width W gradually increases going from the proximal side toward the distal side in relation to the i type semiconductor layer 24.

Also, the relative dielectric constant of the dielectric material constituting the dielectric layer 25 is preferably 20 or greater, and more preferably 30 or greater and 200 or less.

As this kind of dielectric material (high dielectric constant material), examples include nitrogen-added hafnium aluminate (relative dielectric constant: 20), hafnium oxide (relative dielectric constant: 23), yttrium oxide (relative dielectric constant: 25), lanthanum oxide (relative dielectric constant: 27), niobium pentoxide (relative dielectric constant: 41), titanium dioxide (rutile) (relative dielectric constant: 80), and titanium oxide (relative dielectric constant: 160) and the like.

Also, the relative dielectric constant of the structural material of the covering layer 26 is preferably lower than the relative dielectric constant of the dielectric material constituting the dielectric layer 25, and is more preferably lower than the relative dielectric constant of the semiconductor material constituting the i type semiconductor layer 24. With this configuration, it is possible for the terahertz waves to be efficiently led by the dielectric layer 25.

Also, the relative dielectric constant of the structural material of the covering layer 26 is preferably 20 or less, and more preferably 2 or greater and 10 or less.

As this kind of covering layer 26 structural material (low dielectric constant material), examples include polyimide (relative dielectric constant: 3), a borazine compound (relative dielectric constant: 2.3), SiN (relative dielectric constant: 7), $SiO_2$ (relative dielectric constant: 4), hydrogenated siloxane (relative dielectric constant: 3), benzocyclobutene (relative dielectric constant: 2.7), fluorine based resin (relative dielectric constant: 2.7) and the like.

A power supply device 18 is electrically connected to the electrodes 28 and 29 respectively via a pad, conducting wire, connector or the like (not illustrated), and direct current voltage is applied between the electrode 28 and the electrode 29 so that the electrode 28 side is positive.

Next, the operation of the terahertz wave generating device 1 will be described.

With the terahertz wave generating device 1, first, light pulses are generated by the light pulse generator 4 of the light source device 3. The pulse width of the light pulses generated by the light pulse generator 4 is larger than the target pulse width. The light pulses generated by the light pulse generator 4 pass through the waveguide, and pass through the first pulse compressor 5, the amplifier 6, and the second pulse compressor 7 sequentially in that order.

First, at the first pulse compressor 5, pulse compression based on saturable absorption is performed on the light pulses, and the pulse width of the light pulses is decreased. Next, at the amplifier 6, the light pulses are amplified. Finally, at the second pulse compressor 7, pulse compression based on group velocity dispersion compensation is performed on the light pulses, and the pulse width of the light pulses is decreased. In this way, light pulses of the target pulse width are generated, and are emitted from the second pulse compressor 7.

The light pulses emitted from the light source device 3 are irradiated at the aperture 291 of the electrode 29 of the photoconductive antenna 2, and terahertz waves are generated by the i type semiconductor layer 24. These terahertz waves are made incident from the side surface of the i type semiconductor layer 24 to the dielectric layer 25, they advance inside the dielectric layer 25, and are led in a designated direction by the dielectric layer 25. Also, the terahertz waves that advanced inside the dielectric layer 25 are reflected by the electrode 29 and the reflective layer 27, and are prevented from leaking from the top surface or bottom surface of the dielectric layer 25 (lamination direction surface), and with this configuration, it is possible for the terahertz waves to be led efficiently.

As described above, with this terahertz wave generating device 1, the terahertz waves generated by the i type semiconductor layer 24 are led in a designated direction by the dielectric layer 25, and with this configuration, they have directionality. As a result, it is possible to generate high intensity terahertz waves.

Also, the light source 3 has the first pulse compressor 5, the amplifier 6, and the second pulse compressor 7, so it is possible to generate light pulses of desired wave height and desired pulse width while attempting to make the light source device 3 more compact, and thus the terahertz wave generating device 1 more compact, and with this configuration, it is possible to reliably generate the desired terahertz waves.

Embodiment of Imaging Device

Figure 6:
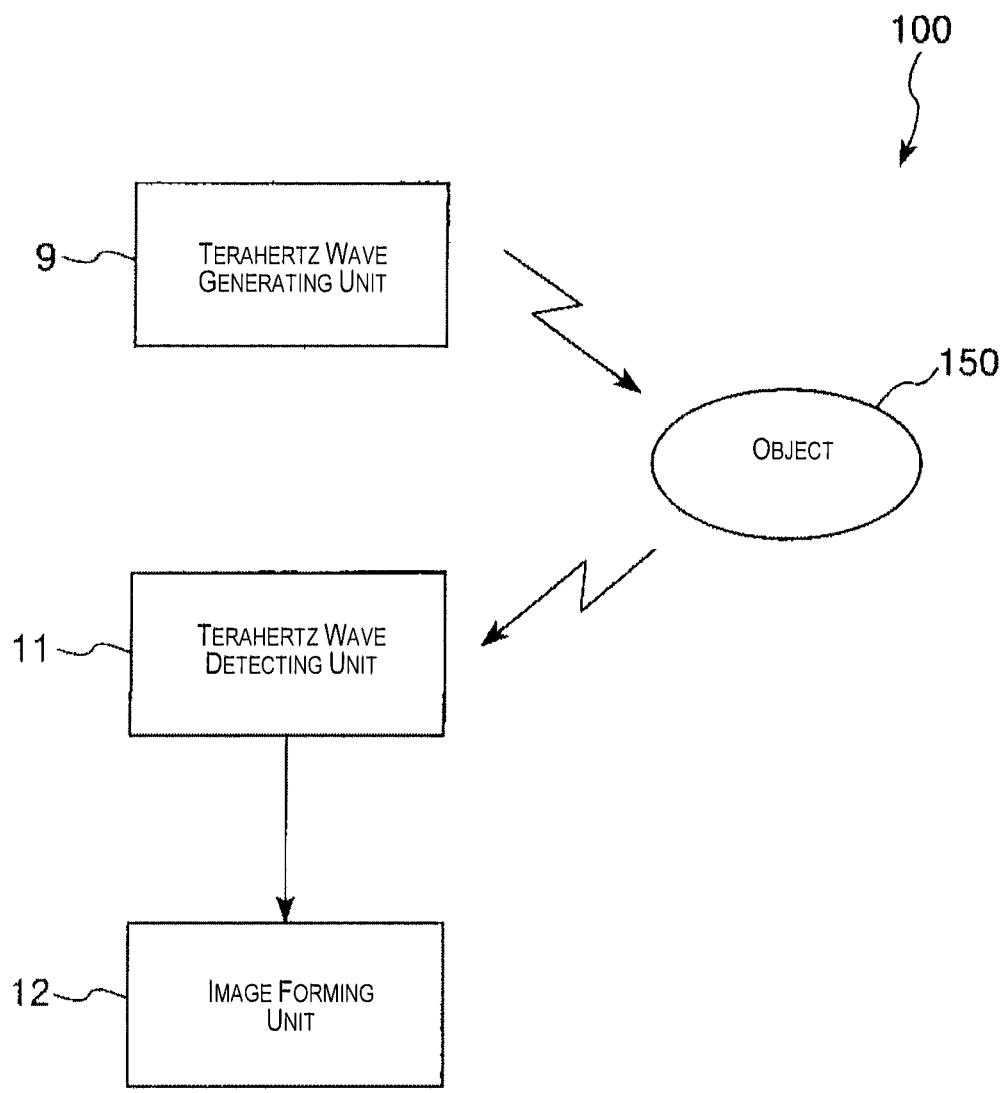
FIG. 6 is a block diagram showing an embodiment of the imaging device of the present invention.
Figure 7:
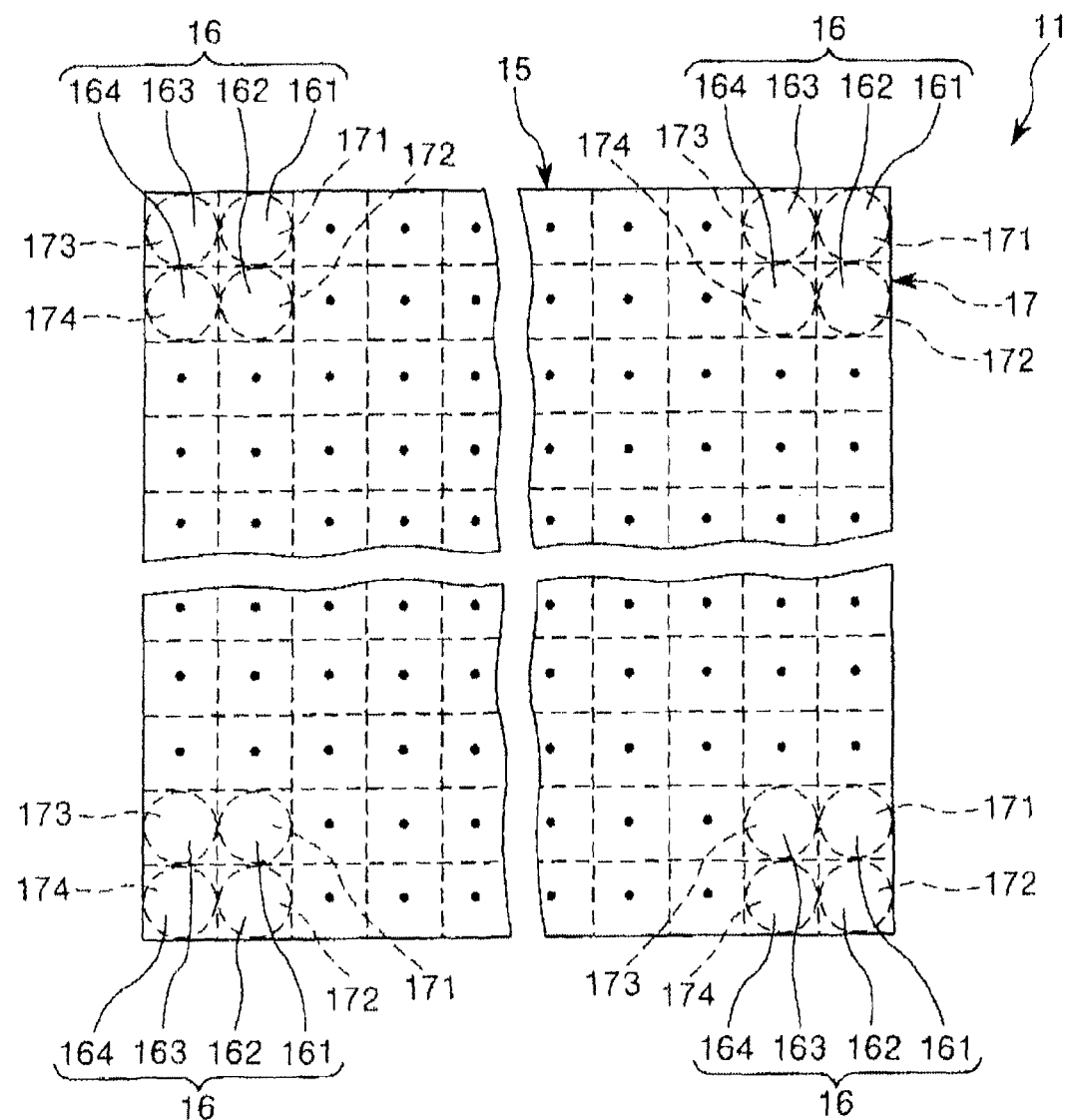
FIG. 7 is a plan view showing the terahertz wave detecting unit of the imaging device shown in FIG. 6.
Figure 8:
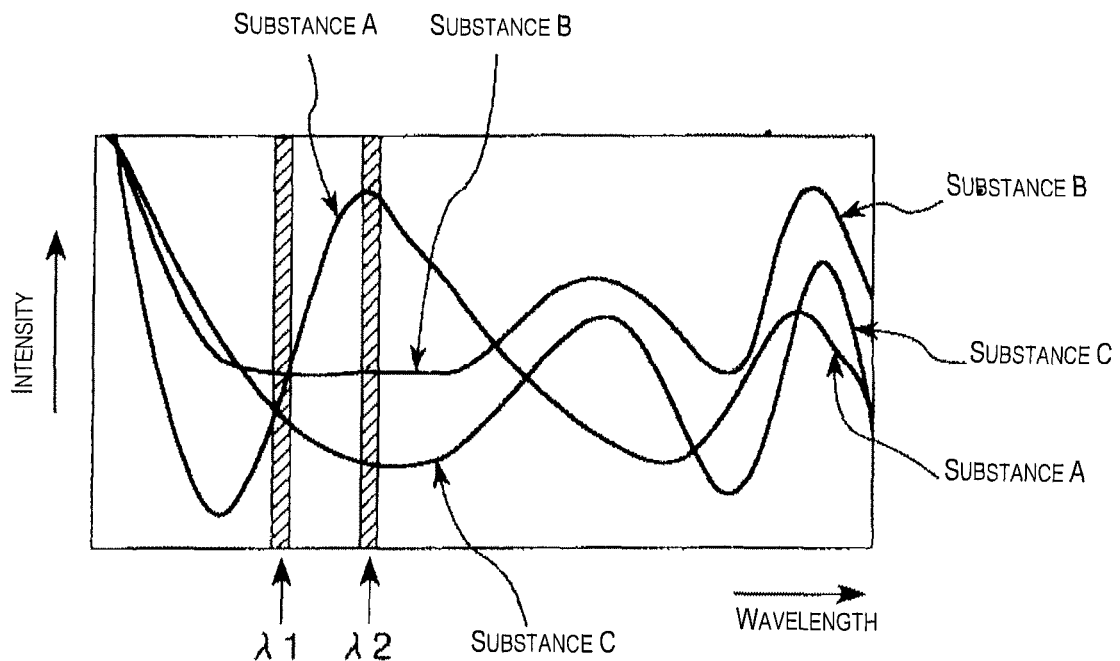
FIG. 8 is a graph showing the spectrum in the terahertz band of the object.
Figure 9:
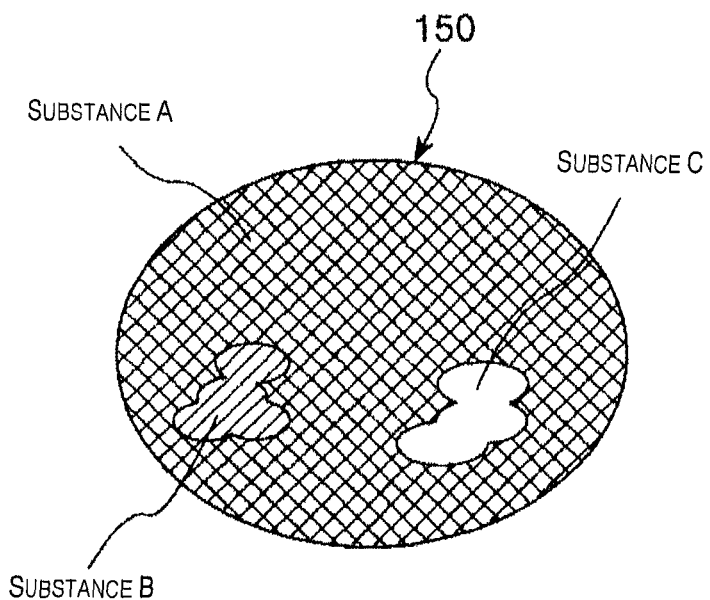
FIG. 9 is a drawing of the image showing the distribution of substances A, B, and C of the object.

FIG. 6 is a block diagram showing an embodiment of the imaging device of the present invention. FIG. 7 is a plan view showing the terahertz wave detecting unit of the imaging device shown in FIG. 6. FIG. 8 is a graph showing the spectrum of the terahertz band of the object. FIG. 9 is a drawing of an image showing the distribution of the substances A, 13, and C of the object.

As shown in FIG. 6, the imaging device 100 is equipped with a terahertz wave generating unit 9, a terahertz wave detecting unit 11 for detecting terahertz waves emitted from the terahertz wave generating unit 9 and passed through or reflected by the object 150, and an image forming unit 12 that generates an image of the object 150, specifically, image data, based on the detection results of the terahertz wave detecting unit 11. The configuration of the terahertz wave generating unit 9 is the same as the previously noted terahertz wave generating device 1, so a description of the terahertz wave generating unit 9 will be omitted.

Also, as the terahertz wave detecting unit 11, an item is used that is equipped with a filter 15 that transmits terahertz waves of target wavelengths, and a detection unit 17 that detects the terahertz waves of the target wavelengths transmitted by the filter 15 and detects them. Also, as the detection unit 17, for example, an item is used that converts terahertz waves to heat and detects it, specifically, an item that converts terahertz waves to heat, and detects the energy (intensity) of the terahertz waves. As this kind of detection unit, examples include pyroelectric sensors, bolometers and the like. Naturally, the terahertz wave detecting unit 11 is not restricted to an item of this constitution.

Also, the filter 15 has a plurality of pixels (unit filter units) 16 arranged two dimensionally. Specifically, the pixels 16 are arranged in matrix form.

Also, the pixels 16 have a plurality of fields that transmit terahertz waves of mutually different wavelengths, specifically, a plurality of fields that have mutually different transmitted terahertz wavelengths (hereafter also called "transmission wavelengths"). With the constitution in the drawing, each pixel 16 has a first field 161, a second field 162, a third field 163, and a fourth field 164.

Also, the detection unit 17 has a first unit detecting unit 171, a second unit detecting unit 172, a third unit detecting unit 173, and a fourth unit detecting unit 174 provided respectively corresponding to the first field 161, second field 162, third field 163, and fourth field 164 of each pixel 16 of the filter 15. Each first unit detecting unit 171, second unit detecting unit 172, third unit detecting unit 173, and fourth unit detecting unit 174 respectively convert to heat and detect terahertz waves that were transmitted through the first field 161, the second field 162, the third field 163, and the fourth field 164 of each pixel 16. As a result, at each respective pixel 16, it is possible to reliably detect the terahertz waves of four target wavelengths.

Next, a use example of the imaging device 100 will be described.

First, the object 150 that is the subject of spectral imaging is constituted by three substances A, B, and C. The imaging device 100 performs spectral imaging of this object 150. Also, here, as an example, the terahertz wave detecting unit 11 detects terahertz waves reflected by the object 150.

With each pixel 16 of the filter 15 of the terahertz wave detecting unit 11, a first field 161 and a second field 162 are used.

Also, when the transmission wavelength of the first field 161 is λ1 and the transmission wavelength of the second field 162 is λ2, and the intensity of the wavelength λ1 component of the terahertz wave reflected by the object 150 is α1 and the intensity of the transmission wavelength λ2 component is α2, the transmission wavelength λ1 of the first field 161 and the transmission wavelength λ2 of the second field 162 are set so that the difference (α2−α1) between the intensity α2 and intensity α1 can be clearly mutually distinguished for the substance A, substance B, and substance C.

As shown in FIG. 8, with substance A, the difference between the intensity α2 of the wavelength λ2 component of the terahertz waves reflected by the object 150 and the intensity α1 of the wavelength λ1 component (α2−α1) is a positive value.

With substance B, the difference between intensity α2 and intensity α1 (α2−α1) is zero.

With substance C, the difference between intensity α2 and intensity α1 (α2−α1) is a negative value.

With the imaging device 100, when performing spectral imaging of the object 150, first, terahertz waves are generated by the terahertz wave generating unit 9, and those terahertz waves are irradiated on the object 150. Then, the terahertz wave detecting unit 11 detects the terahertz waves reflected by the object 150 as α1 and α2. These detection results are sent to the image forming unit 12. The detection of irradiation of terahertz waves on the object 150 and terahertz waves reflected by the object 150 is performed for the overall object 150.

The image forming unit 12 finds the difference α2−α1) between the intensity α2 of the wavelength λ2 component of the terahertz waves transmitted through the second field 162 of the filter 15 and the intensity α1 of the wavelength λ1 component of the terahertz waves transmitted through the first field 161 based on the detection results. Then, of the object 150, sites for which the difference is a positive value are determined and specified as being substance A, sites for which the difference is zero as substance B, and sites for which the difference is a negative value as substance C.

As shown in FIG. 9, the image forming unit 12 creates image data of an image showing the distribution of the substances A, B and C of the object 150. This image data is sent to a monitor (not illustrated) from the image forming unit 12, and an image showing the distribution of the substance A, substance B, and substance C of the object 150 is displayed on the monitor. In this case, for example, color coded display is done so that the field in which substance A of the object 150 is distributed is shown as black, the field in which substance B is distributed is shown as gray, and the field in which substance C is distributed is shown as white. With this imaging device 100, as described above, it is possible to identify each substance constituting the object 150 and to simultaneously perform distribution measurement of each substance.

The application of the imaging device 100 is not limited to the item described above, and for example, it is possible to irradiate terahertz waves on a person, to detect terahertz waves transmitted or reflected by that person, and by performing processing at the image forming unit 12, it is possible to determine whether that person is holding a gun, knife, illegal drugs or the like.

Embodiment of Measuring Device

Figure 10:
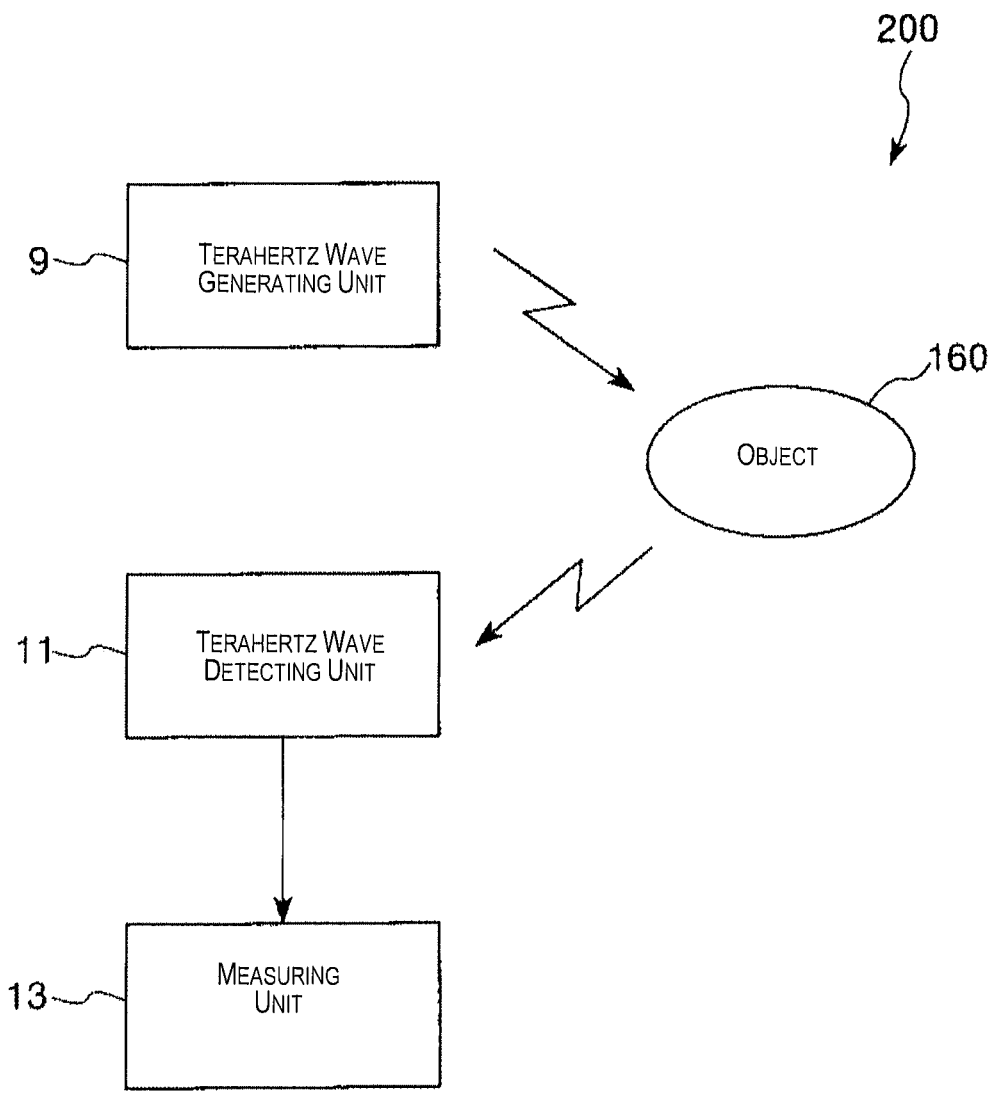
FIG. 10 is a block diagram showing an embodiment of the measuring device of the present invention.

FIG. 10 is a block diagram showing an embodiment of the measuring device of the present invention.

Following, the description of the embodiment of the measuring device will focus on the differences from the previously described embodiment of the imaging device, the same items will be given the same code numbers, and a detailed description of those will be omitted.

As shown in FIG. 10, the measuring device 200 is equipped with a terahertz wave generating unit 9 for generating terahertz waves, a terahertz wave detecting unit 11 for detecting terahertz waves emitted from the terahertz wave generating unit 9 and transmitted through or reflected by the object 160, and a measuring unit 13 for measuring the object 160 based on the detection results of the terahertz wave detecting unit 11.

Next, a use example of the measuring device 200 will be described.

With the measuring device 200, when performing spectroscopic measurement of the object 160, first, terahertz waves are generated by the terahertz wave generating unit 9, and those terahertz waves are irradiated on the object 160. Then, the terahertz waves transmitted by or reflected by the object 160 are detected by the terahertz wave detecting unit 11. These detection results are sent to the measuring unit 13. Irradiation of the terahertz waves on the object 160 and detection of the terahertz waves transmitted by or reflected by the object 160 are performed for the overall object 160.

With the measuring unit 13, from the detection results, the respective intensities of the terahertz waves that were transmitted through the first field 161, the second field 162, the third field 163, and the fourth field 164 of the filter 15 are found out, and analysis or the like of the object 160 components and their distribution is performed.

Embodiment of Camera

Figure 11:
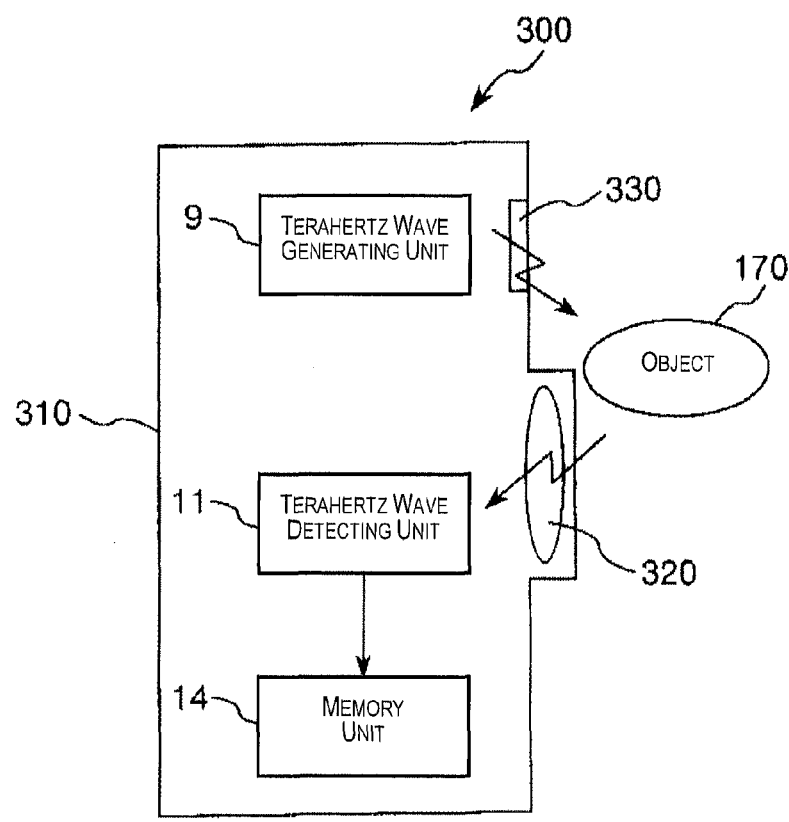
FIG. 11 is a block diagram showing an embodiment of the camera of the present invention.

FIG. 11 is a block diagram showing the embodiment of the camera of the present invention. Also, FIG. 12 shows a schematic perspective view showing an embodiment of the camera of the present invention.

Following, the description of the embodiment of the camera will focus on the differences from the previously described embodiment of the image device, the same items are given the same code numbers as in the previously described embodiments, and a detailed description of those will be omitted.

Figure 12:
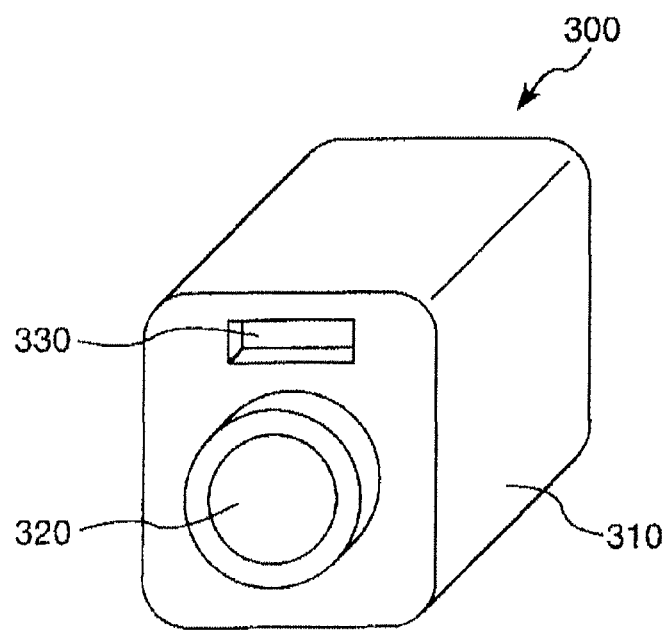
FIG. 12 is a perspective view showing an embodiment of the camera of the present invention.

As shown in FIG. 11 and FIG. 12, the camera 300 is equipped with a terahertz wave generating unit 9 for generating terahertz waves, a terahertz wave detecting unit 11 for detecting terahertz waves emitted from the terahertz wave generating unit 9 and reflected by the object 170, and a memory unit 14. Then, each of these parts is housed in a case 310 of the camera 300. Also, the camera 300 is equipped with a lens (optical system) 320 for converging (imaging) the terahertz waves reflected by the object 170 on the terahertz wave detecting unit 11, and a window part 330 for emitting to outside the case 310 the terahertz waves generated by the terahertz wave generating unit 9. The lens 320 and the window part 330 are constituted by members using silicon, quartz, polyethylene or the like that transmit or refract terahertz waves. The window part 330 can also be constituted with an aperture simply provided as a slit.

Next, a use example of the camera 300 will be described.

With the camera 300, when taking an image of the object 170, first, terahertz waves are generated by the terahertz wave generating unit 9, and those terahertz waves are irradiated on the object 170. Then, the terahertz waves reflected by the object 170 are converged (imaged) by the lens 320 to the terahertz wave detecting unit 11 and detected. The detection results are sent to and stored in the memory unit 14. Detection of irradiation of the terahertz waves on the object 170 and of the terahertz waves reflected by the object 170 is performed on the overall object 170. The detection results can also be sent to an external device such as a personal computer or the like, for example. With the personal computer, it is possible to perform various processes based on the detection results.

Above, the photoconductive antenna, the terahertz wave generating device, the camera, the imaging device, and the measuring device according to the present invention were described based on the embodiments in the drawings, but the present invention is not limited to this, and the constitution of each part can be replaced with an item of any constitution having the same functions. It is also possible to add any other constituent materials to the present invention.

Also, with the aforementioned embodiments, an n type semiconductor layer was used as the first conductive layer, and a p type semiconductor layer was used as the second conductive layer, but with the present invention, this is not restricted to these, and it is also possible to use a p type semiconductor layer for the first conductive layer and an n type semiconductor layer for the second conductive layer.

Also, with the present invention, the light pulse generator can be a separate item from the light source device.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A photoconductive antenna adapted to generate terahertz waves when irradiated by pulsed light, the photoconductive antenna comprising:
   a first conductive layer made of a semiconductor material containing a first conductive type impurity;
   a second conductive layer made of a semiconductor material containing a second conductive type impurity different from the first conductive type impurity;
   a semiconductor layer positioned between the first conductive layer and the second conductive layer in a lamination direction in which the first conductive layer, the semiconductor layer, and the second conductive layer are stacked, the semiconductor layer being made of a semiconductor material having a carrier density that is lower than a carrier density of the semiconductor material of the first conductive layer or a carrier density of the semiconductor material of the second conducive layer;
   a first electrode electrically connected to the first conductive layer;
   a second electrode electrically connected to the second conductive layer, and having an aperture through which the pulsed light passes; and
   a dielectric layer made of a dielectric material, and being in contact with a surface of the semiconductor layer having a normal direction extending orthogonal to the lamination direction, the dielectric layer having first and second edges that define an outer periphery of the dielectric layer as viewed in the lamination direction such that a width between the first and the second edges as viewed in the lamination direction gradually increases as a distance between the width and the semiconductor layer increases.

2. The photoconductive antenna according to claim 1, wherein
   a relative dielectric constant of the dielectric material is higher than a relative dielectric constant of the semiconductor material of the semiconductor layer.

3. The photoconductive antenna ac cording to claim 1, further comprising
   a covering layer covering a part of the surface of the semiconductor layer which is not in contact with the dielectric layer.

4. The photoconductive antenna according to claim 1, further comprising
   a first reflective layer in contact with a bottom surface of the dielectric layer, and configured and arranged to reflect the terahertz waves.

5. The photoconductive antenna according to claim 1, wherein
   the first electrode is configured and arranged to reflect the terahertz waves.

6. The photoconductive antenna according to claim 1, further comprising
   a second reflective layer in contact with a top surface of the dielectric layer, and configured and arranged to reflect the terahertz waves.

7. The photoconductive antenna according to claim 1, wherein
   the second electrode is configured and arranged to reflect the terahertz waves.

8. The photoconductive antenna according to claim 1, wherein
   the second conductive layer includes a thin walled part having a thickness in the lamination direction that is thinner than a part of the second conductive layer disposed outside of the aperture as viewed along the lamination direction.

9. The photoconductive antenna according to claim 1, wherein
   the semiconductor material of the semiconductor layer is a III-V compound.

10. A terahertz wave generating device comprising:
    the photoconductive antenna according to claim 1; and
    a light source configured and arranged to generate the pulsed light.

11. A terahertz wave generating device comprising:
    the photoconductive antenna according to claim 2; and
    a light source configured and arranged to generate the pulsed light.

12. A camera comprising:
the photoconductive antenna according to claim 1;
a light source configured and arranged to generate the pulsed light; and
a terahertz wave detecting unit configured and arranged to detect the terahertz waves emitted from the photoconductive antenna and reflected by an object.

13. A camera comprising:
the photoconductive antenna according to claim 2;
a light source configured and arranged to generate the pulsed light; and
a terahertz wave detecting unit configured and arranged to detect the terahertz waves emitted from the photoconductive antenna and reflected by an object.

14. An imaging device comprising:
the photoconductive antenna according to claim 1;
a light source configured and arranged to generate the pulsed light;
a terahertz wave detecting unit configured and arranged to detect the terahertz waves emitted from the photoconductive antenna and transmitted through an object or reflected by the object; and
an image forming unit configured and arranged to generate an image of the object based on detection results of the terahertz wave detecting unit.

15. The imaging device according to claim 14, wherein
the image forming unit is configured and arranged to generate the image of the object using intensity of the terahertz waves detected by the terahertz wave detecting unit.

16. An imaging device comprising:
the photoconductive antenna according to claim 2;
a light source configured and arranged to generate the pulsed light;
a terahertz wave detecting unit configured and arranged to detect the terahertz waves emitted from the photoconductive antenna and transmitted through an object or reflected by the object; and
an image forming unit configured and arranged to generate an image of the object based on detection results of the terahertz wave detecting unit.

17. The imaging device according to claim 16, wherein
the image forming unit is configured and arranged to generate the image of the object using intensity of the terahertz waves detected by the terahertz wave detecting unit.

18. A measuring device comprising:
the photoconductive antenna according to claim 1;
a light source configured and arranged to generate the pulsed light;
a terahertz wave detecting unit configured and arranged to detect the terahertz waves emitted from the photoconductive antenna and transmitted through an object or reflected by the object; and
a measuring unit configured and arranged to measure the object based on detection results of the terahertz wave detecting unit.

19. The measuring device according to claim 18, wherein
the measuring unit is configured and arranged to measure the object using intensity of the terahertz waves detected by the terahertz wave detecting unit.

20. A measuring device comprising:
the photoconductive antenna according to claim 2;
a light source configured and arranged to generate the pulsed light;
a terahertz wave detecting unit configured and arranged to detect the terahertz waves emitted from the photoconductive antenna and transmitted through an object or reflected by the object; and
a measuring unit configured and arranged to measure the object based on detection results of the terahertz wave detecting unit.

21. The measuring device according to claim 20, wherein
the measuring unit is configured and arranged to measure the object using intensity of the terahertz waves detected by the terahertz wave detecting unit.

\* \* \* \* \*